." Patent Number: 5,053,403
Date of Patent: Oct. 1, 1991

United States Patent [19]
Orentreich et al.

[54] METHODS FOR TREATMENT OF MALE-PATTERN BALDNESS

[75] Inventors: Norman Orentreich, 140 E 72, New York; Jonathan R. Matias, Richmond Hill, N.Y.

[73] Assignee: Norman Orentreich, New York, N.Y.

[21] Appl. No.: 438,979

[22] Filed: Nov. 20, 1989

Related U.S. Application Data

[60] Continuation of Ser. No. 79,609, Jul. 30, 1987, abandoned, which is a division of Ser. No. 846,498, Mar. 27, 1986, Pat. No. 4,684,635, which is a continuation of Ser. No. 609,152, May 11, 1984, abandoned.

[51] Int. Cl.$^5$ .............................................. A61K 31/56
[52] U.S. Cl. ................................... 514/170; 514/171; 514/175; 514/177; 514/178; 514/181
[58] Field of Search ............... 514/170, 171, 175, 177, 514/178, 181

[56] References Cited

U.S. PATENT DOCUMENTS 4,684,635  8/1987  Orentreich et al. ................. 514/170

OTHER PUBLICATIONS

Aron-Brunetiere–"Aspects of Endocrinological Treatment", Hair Research (1981) pp. 312–317.
Matias, J. R., Malloy, V. & Orentreich, N., "Animal Models of Androgen-Dependent Disorders of the Pilosebaceous Apparatus," *Arch. Dermatol. Res.*, 281: 247–53 (1989).
Nielsen,. P. G., "Treatment of Moderate Idiopathic Hirsutism with a Cream Containing Canrenone" (an Antiandrogen), *Dermatologica*, 165, pp. 636–639 (1982).
Rentoul, J. R., "Management of the Hirsute Woman," *Intl. J. Derm.*, 22, pp. 265–72 (1983).

*Primary Examiner*—Leonard Schenkman
*Attorney, Agent, or Firm*—Panitch Schwarze Jacobs & Nadel

[57] ABSTRACT

Synergistic compositions for inhibiting the action of androgens comprise the combination in a single topical preparation of a 5α-reductase enzyme inhibitor and an androgen receptor blocking agent in a pharmaceutically and dermatologically acceptable vehicle. The compositions may be topically applied to affected areas of the skin in the treatment or prevention of sebaceous gland hypertrophy, hirsutism and male-pattern baldness in mammals. The inhibitor and blocking agent are present in the composition in a weight ratio of about 1:20 to 5:1, with the inhibitor comprising up to about 0.1% w/v of the comopsition and the blocking agent comprising up to about 1% w/v of the composition.

9 Claims, No Drawings

METHODS FOR TREATMENT OF MALE-PATTERN BALDNESS

This is a continuation of Ser. No. 07/079,609, 07/30/87 abandoned which is a division, of application Ser. No. 846,498, now U.S. Pat. No. 4,684,635, filed Mar. 27, 1986, which is a continuation of application Ser. No. 609,152, filed May 11, 1984 abandoned.

FIELD OF THE INVENTION

The present invention relates to compositions and methods for inhibiting the action of androgens. More particularly, the invention is directed to synergistic combinations of a 5α-reductase enzyme inhibitor and an androgen receptor blocking agent for topical applications to the skin in the treatment and prevention of sebaceous gland hypertrophy, hirsutism and male-pattern baldness.

BACKGROUND OF THE INVENTION

The development of acne, hirsutism and male-pattern baldness is dependent upon the presence of androgens, particularly testosterone and dihydrotestosterone (DHT). Testosterone is secreted into the blood stream by the adrenals and gonads and enters the cells of the sebaceous glands or hair follicles. This steroid binds specifically to the 5α-reductase enzyme which converts testosterone to its most active metabolite DHT. DHT binds to specific receptor proteins in the cell cytoplasm, and this steroid-protein complex is translocated to the nucleus of the cell where DHT becomes bound to the nuclear receptor protein. Nuclear binding is followed by the synthesis of specific classes of proteins, eventually leading to hypertrichosis (hirsutism), alopecia (male-pattern baldness) or sebaceous gland hypertrophy (manifested as acne or other skin inflammations).

The inhibition of testosterone conversion to DHT by the 5α-reductase enzyme and the inhibition of DHT binding to the receptor protein are accepted therapeutic modalities. A number of compounds, called antiandrogens, have been developed which can interfere with either testosterone metabolism or DHT binding to the receptor.

The serious side effects (such as decreased libido) produced by the systemic administration of antiandrogens preclude the systemic use of these drugs for the treatment of the above skin disorders. For example, progesterone is a highly active 5α-reductase enzyme inhibitor, but systemically disturbs the menstrual cycle in women, since it must be used on a regular basis in order to be effective. Many studies have shown that individual antiandrogens can be used topically to inhibit the action of androgens. However, applicants are not aware of any prior studies on the effectiveness of combining 5α-reductase inhibitors with androgen receptor blocking agents in a topical preparation.

BRIEF SUMMARY OF THE INVENTION

It has been discovered that certain combinations of a 5α-reductase enzyme inhibitor and an androgen receptor blocking agent have a synergistic effect in the inhibition of the action of androgens particularly in the treatment and prevention of sebaceous gland hypertrophy, hirsutism and male-pattern baldness. The compositions of the invention are applied topically to affected areas of the skin of humans and other mammals in therapeutically effective amounts. These combinations of inhibitors and blocking agents at certain concentrations and ratios act synergistically to produce a marked inhibition of the effects of the endogenous androgens on the skin. The steroid combinations may be delivered through the skin by means of various topical vehicles.

DETAILED DESCRIPTION OF THE PREFERRED EMBODIMENT

There are a number of steroids, steroid precursors and derivatives which are known to be effective as 5α-reductase inhibitors and which may be used in the compositions of the present invention. These include progesterone, 17β-carboxylic acid derivatives of testosterone, desoxycorticosterone, desoxycorticosterone acetate, 19-nor-testosterone, 4-pregnen-20β-ol-3-one and 17α-hydroxyprogesterone. Of these, progesterone is preferred since it is the most active inhibitor and has been shown to be topically effective by itself.

Both steroidal and non-steroidal androgen receptor blocking agents (blockers or inhibitors) may be used in the synergistic compositions of the present invention. Representative examples of steroidal blocking agents include spironolactone, cyproterone acetate, trimethyltrienolone (available from Roussel Uclaf under the designation RU 2956), canrenone and canrenoic acid. Examples of suitable non-steroidal blocking agents include flutamide (α,α,α-trifluoro-2-methyl-4'-nitro-m-propionotoluide) and hydroxy-flutamide (α,α,α-trifluoro-2-methyl-4'-nitro-m-lactoluidide), both available from Schering Corp., and RU 23908 (5,5-dimethyl-3-[4-nitro-3(trifluoromethyl)phenyl]-2,4-imidazolidinedione) and RU 22930 (5,6-dihydro-2-methyl-4-[4-nitro-3-(trifluoromethyl)phenyl]-2H-1,2,4-oxadiozin-3-(4H)-one, available from Roussel Uclaf.

Generally, the ratios of 5α-reductase inhibitor to androgen receptor blocking agent which have been found to be effective in the compositions of the present invention range between about 1:20 and 5:1. Ratios of about 1:1 to 2:1 are preferred.

It has also been found that the synergistic effects of the combinations of the present invention are most pronounced at relatively low concentrations of the 5α-reductase inhibitor and androgen receptor blocker. In particular, optimal concentrations for the 5α-reductase inhibitors appear to range from about 0.005% to 0.1% weight/volume of the total composition, while optimal concentrations for the androgen receptor blockers appear to range from about 0.01% to 0.5% weight/volume of the total composition. Concentrations below about 0.005 5α-reductase inhibitor and about 0.01 androgen receptor blocker give very little antiandrogenic response. Concentrations above about 0.1% 5α-reductase inhibitor and about 0.5% androgen receptor blocker are not only unnecessarily wasteful, expensive and liable to produce adverse side effects, but were also found to have very little synergistic effect above that obtained by applying either the 5α-reductase inhibitor or the androgen receptor blocker alone.

It has been found according to the present invention that when a 5α-reductase inhibitor is applied together with an androgen receptor blocker as a single topical preparation, the resulting inhibition of androgens was greater than the sum total of the effects produced independently by the 5α-reductase inhibitor and the androgen receptor blocker.

These effects will now be demonstrated and described in more detail with reference to the following specific, non-limiting examples. The hamster ear sebaceous gland was selected as a test model because of the similarities in morphology to human sebaceous glands and in all turnover time. It is well accepted in the medical literature that antiandrogens which work to inhibit sebaceous glands by topical means should also work to inhibit the androgenic effects in the hair follicle. Thus, the mechanism of androgenic control is similar for sebaceous gland hypertrophy, hirsutism and androgenic alopecia.

EXAMPLE NOS. 1-12

A series of experiments were carried out using 5 or 6 animals for each data point. The various concentrations of 5α-reductase inhibitor or androgen receptor blocker is considered an insignificant inhibition of androgenic effects on sebaceous glands.

The data in Table I demonstrate that each combination of 5α-reductase inhibitor and androgen receptor blocker produces a synergistic effect as compared to the effects of 5α-reductase inhibitor and androgen receptor blocker alone. That is, the sum of the individual inhibitory activities (100 minus androgenic activity) of the 5α-reductase inhibitor and androgen receptor blocker is considerably less than the inhibitory activity of the combined composition of 5α-reductase inhibitor and androgen receptor blocker. Such reductions in androgen activity correlate very well to inhibition of acne, hirsutism and male-pattern baldness.

TABLE I
THE SYNERGISTIC EFFECTS OF VARIOUS COMBINATIONS OF 5α-REDUCTASE AND ANDROGEN RECEPTOR INHIBITORS

| | EFFECT OF 5α-REDUCTASE INHIBITOR ALONE | | COMBINED | EFFECT OF ANDROGEN RECEPTOR BLOCKER ALONE | | |
|---|---|---|---|---|---|---|
| 5α-REDUCTASE INHIBITOR | CONCENTRATION (% w/v) | % OF CONTROL GLAND SIZE | % OF CONTROL GLAND SIZE | % OF CONTROL GLAND SIZE | CONCENTRATION (% w/v) | ANDROGEN RECEPTOR INHIBITOR |
| PROGESTERONE | 0.05 | 92 | 60 | 85 | 0.5 | SPIRONOLACTONE |
| PROGESTERONE | 0.10 | 77 | 57 | 92 | 0.1 | SPIRONOLACTONE |
| PROGESTERONE | 0.05 | 92 | 65 | 92 | 0.1 | SPIRONOLACTONE |
| PROGESTERONE | 0.010 | 100 | 65 | 92 | 0.1 | SPIRONOLACTONE |
| PROGESTERONE | 0.005 | 100 | 73 | 92 | 0.1 | SPIRONOLACTONE |
| PROGESTERONE | 0.05 | 92 | 75 | 86 | 0.05 | SPIRONOLACTONE |
| PROGESTERONE | 0.025 | 100 | 52 | 86 | 0.05 | SPIRONOLACTONE |
| PROGESTERONE | 0.010 | 100 | 74 | 92 | 0.05 | SPIRONOLACTONE |
| PROGESTERONE | 0.005 | 100 | 85 | 100 | 0.010 | SPIRONOLACTONE |
| PROGESTERONE | 0.05 | 92 | 68 | 81 | 0.05 | FLUTAMIDE |
| PROGESTERONE | 0.05 | 92 | 54 | 93 | 0.05 | TRIMETHYLTRIENOLONE |
| PROGESTERONE | 0.05 | 92 | 66 | 94 | 0.05 | CYPROTERONE ACETATE | or both as shown in Table I where each dissolved in acetone and 25 μl of each solution was applied unilaterally on the right ventral ear skin of adult male Syrian hamsters two times a day, five days per week for a total duration of four weeks. Control animals received topical applications of acetone alone. At the end of the experiment, the androgen-sensitive ear skin sebaceous glands of the hamsters were analyzed according to the method of Matias and Orentriech, *Journal of Investigative Dermatology*, 81:43 (1983), with minor modifications. In brief, the ventral ear skin was manually separated from the cartilage and stained for three hours with 0.1% Sudan Black in propylene glycol. After rinsing overnight with 85% propylene glycol, a defined area (medial zone; 5-8 mm from the apex of the ear) was biopsied. The darkly stained sebaceous glands were visualized from the underside at a magnification of 625X and quantitated planimetrically using a graphics computer interfaced with the microscope.

The size of the sebaceous glands taken as above from the right ventral ear of each hamster was compared with similar samples taken from the acetone treated right ventral ear of another group of hamsters as controls. The effects of the various inhibitors, as measured by sebaceous glands size, are given in Table I as a percent of the size of the vehicle treated control group. That is, 100% means that the treated ear sebaceous glands were the same size as the sebaceous glands of the vehicle treated control ears, and hence there was no inhibition of androgenic activity. On the other hand, an androgenic activity of 60% means that the sebaceous gland size of the treated ear was 60% of the size of the sebaceous glands of the vehicle treated control ear, thus indicating a 40% decrease in androgenic activity. Generally, a percent activity between about 90% and 100%

The compositions of the present invention may be applied in any of a wide variety of topical application forms, including solutions such as the acetone solution used in the examples above, tinctures, creams, ointments, gels, lotions or aerosol sprays. Such preparations may be either alcohol- or water-based or a combination of alcohol/water base. Typical examples of topical preparations according to the present invention are set forth in Examples 13-18 below.

EXAMPLE 13
Solution

| | % w/v |
|---|---|
| Progesterone | 0.025 |
| Spironolactone | 0.05 |
| Acetone | QS |
| | 100.0 |

EXAMPLE 14
Tincture

| | % w/v |
|---|---|
| Progesterone | 0.025 |
| Canrenone | 0.05 |
| Propylene glycol | 10.0 |
| Wager | 24.0 |
| Alcohol | QS |
| | 100.0 |

EXAMPLE 15

Cream

| | % w/v |
|---|---|
| Desoxycorticosterone | 0.025 |
| Trimethyltrienolone | 0.05 |

Oil Phase

| | |
|---|---|
| Petrolatum | 10.0 |
| Stearyl alcohol | 4.0 |
| Polyethylene glycol monostearate | 4.0 |
| Stearic acid | 2.0 |

Water Phase

| | |
|---|---|
| Glycerin | 5.0 |
| Triethanolamine | 1.0 |
| Preservative (methyl and Propyl parabens) | 0.2 |
| Water | QS |
| | 100.0 |

EXAMPLE 16

Ointment

| | % w/v |
|---|---|
| Progesterone | 0.025 |
| Flutamide | 0.05 |
| Propylene glycol | 12.0 |
| Sorbitan sesquioleate | 4.0 |
| Petrolatum | QS |
| | 100.0 |

EXAMPLE 17

Gel

| | % w/v |
|---|---|
| Desoxycorticosterone acetate | 0.025 |
| Non-steroidal antiandrogen RU 23908) | 0.05 |
| Carbomer 940 | 1.0 |
| Triethanolamine | 0.4 |
| Isopropyl myristate | 5.0 |
| Water | 35.0 |
| Alcohol | QS |
| | 100.0 |

EXAMPLE 18

Aerosol Lotion

| | % w/v |
|---|---|
| Progesterone | 0.025 |

-continued

| | % w/v |
|---|---|
| Canrenoic acid | 0.05 |
| Polyethylene glycol monostearate | 2.0 |
| Myristyl myristate | 2.0 |
| Polysorbate 20 | 1.0 |
| Water | QS |
| Alcohol | 12.0 |
| Dimethyl ether propellant | 10.0 |
| Fluorohydrocarbon propellant | 10.0 |
| | 100.0 |

It will be recognized by those skilled in the art that changes may be made to the above-described embodiments of the invention without departing from the broad inventive concepts thereof. It is understood, therefore, that this invention is not limited to the particular embodiments disclosed, but it is intended to cover all modifications which are within the scope and spirit of the invention as defined by the appended claims.

We claim:

1. A method for treating male-pattern baldness in mammals comprising topically applying to the affected areas of the skin therapeutically and synergistically effective amounts of a composition comprising (a) an inhibitor of the conversion of testosterone to dihydrotestosterone by the 5α-reductase enzyme, (b) a blocking agent which blocks the binding of dihydrotestosterone to receptor protein in cell cytoplasm, and (c) a pharmaceutically and dermatologically acceptable vehicle for said inhibitor and said blocking agent.

2. A method according to claim 1 wherein said inhibitor and said blocking agent are present in the weight ratio of about 1:20 to 5:1.

3. A method according to claim 1 wherein said inhibitor and said blocking agent are present in the weight ratio of about 1:1 to 1:2.

4. A method according to claim 1 wherein said inhibitor comprises up to about 0.1% and said blocking agent comprises up to about 1.0% of the composition, said percentages being on the basis of weight/volume.

5. A method according to claim 1 wherein said inhibitor is selected from the group consisting of progesterone, 17β-carboxylic acid derivatives of testosterone, desoxycorticosterone, desoxycorticosterone acetate, 19-nortestosterone, 4-pregnen-20β-ol-3-one and 17α-hydroxyprogesterone.

6. A method according to claim 1 wherein said inhibitor is progesterone.

7. A method according to claim 1 wherein said blocking agent is selected from the group consisting of spironolactone, cyproterone acetate, flutamide, trimethyltrienolone, hydroxy-flutamide, canrenone, canrenoic acid, 5,5-dimethyl-3-[4-nitro-3(trifluoromethyl)-phenyl]-2,4-imidazolidinedione and 5,6-dihydro-2-methyl-4-[4-nitro-3-(trifluoromethyl)phenyl]-2H-1,2,4-oxadiozin-3-(4H)-one.

8. A method according to claim 1 wherein said vehicle comprises water, alcohol, acetone, or a combination thereof.

9. A method according to claim 1 wherein said vehicle is selected from the group consisting of solutions, tinctures, creams, ointments gels, lotions and aerosol sprays.

* * * * *